United States Patent

Guarnieri

[11] 4,172,706
[45] Oct. 30, 1979

[54] PROCESS FOR THE QUANTITATIVE AND QUALITATIVE ANALYSES OF ALDEHYDES AND KETONES IN AQUEOUS SOLUTIONS

[76] Inventor: Michael Guarnieri, 6222 Woodcrest Ave., Baltimore, Md. 21209

[21] Appl. No.: 821,770

[22] Filed: Aug. 4, 1977

[51] Int. Cl.$^2$ .................. G01N 33/18; G01N 23/10
[52] U.S. Cl. .................. 23/230.6; 23/230 M; 23/230 R
[58] Field of Search ............. 23/230 R, 230.6, 230 M, 23/230 B

[56] References Cited

U.S. PATENT DOCUMENTS 3,506,402  4/1970  Simon ........................ 23/230.6 X
3,623,840  11/1971  Benson ........................ 23/230.6

Primary Examiner—R. E. Serwin

[57] ABSTRACT

Trace amounts of carbonyl compounds, I, in aqueous solutions are analyzed by mixing the aqueous solution with radioactive derivatives of ammonia, II. Carbonyl compounds stoichiometrically react with derivatives of ammonia as follows

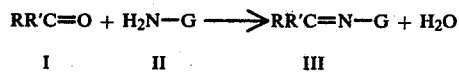

The weight of the parent compound, I is calculated from the radioactivity of the product, III, and the specific activity of II.

The product is separated from the reaction mixture by chromatography or electrophoresis. The identity of I, if unknown, can be determined from the characteristic chromatographic or electrophoretic mobility of the derivative, III.

The sensitivity of the method is determined by the specific activity of the radioactive chemical, II. Thus, if II contains 100 micro curies per micro mole, the process would detect $10^{-12}$ mole of carbonyl compound.

7 Claims, No Drawings

PROCESS FOR THE QUANTITATIVE AND QUALITATIVE ANALYSES OF ALDEHYDES AND KETONES IN AQUEOUS SOLUTIONS

BACKGROUND AND SUMMARY OF THE INVENTION

The invention relates to processes for analyzing aldehydes and ketones in aqueous solutions and in particular to processes for the quantitative and qualitative analyses of such aldehydes and ketones in aqueous solutions. Specifically, a need has existed for an improved method of measuring trace amounts of organic chemicals in aqueous solutions. This invention provides such an improved method for measuring aldehydes and ketones.

Measurements of trace amounts of organic chemicals in aqueous solutions have continually challenged the analytical chemist. The organic compounds must be extracted from the aqueous media, a time consuming process if the chemical is partially soluble in water. Volatile chemicals can be lost during extraction. Gas chromatography and mass spectroscopy have been used to analyze the organic compounds. In certain cases, chemicals are derivatized to enhance their measurement. Derivative formation can also require extensive sample preparations. Despite these problems, the need for accurate measurements of chemical residues in water has increased as we learn more about the effects of pollution on our environment and our health.

This invention provides a significantly new approach to the characterization and measurement of trace amounts of organic molecules in water. Radioactive derivatives of ammonia having high specific activities are used to label carbonyl compounds. The labeled compound is isolated and measured for radioactivity. The sensitivity (limits of detection) of this process are determined by the specific activity of the derivative. For example, 1 mole of acetone mixed with excess hydrazine containing 1 curie per mole would yield a hydrazone containing 1 curie or $10^{12}$ counts per mintue (cpm). An hydrazine containing 100 curie/mole yields a hydrazone containing $10^{14}$ cpm. Because radioactivity measuring devices can measure $10^2$ cpm with accuracy, the latter reaction would detect $10^{-12}$ mole of acetone.

Derivatives of ammonia have been used widely for many years to characterize organic compounds. The chromatographic properties of hundreds of hydrazones, phenylhydrazones, and semicarbazones have been published. Several scientists have used hydrazines to form derivatives for the gravimetric and spectrophotometric quantitation of compounds. Generally, the sensivity of these measurements is low, detecting less than $10^{-6}$ molar amounts. Never have radioactive derivatives of ammonia been used to quantitatively measure carbonyl compounds.

It is, therefore, an object of the invention to provide an improved method for measuring trace amounts of carbonyl compounds in aqueous solutions.

It is another object of the invention to use radioactive derivatives of ammonia, having high specific activities to label carbonyl compounds.

It is still another object of the invention to identify trace amounts of carbonyl compounds by chromatographic or electrophoretic methods.

Further objects and advantages of the invention will become more apparent in light of the following description of the preferred embodiments.

DESCRIPTION OF THE PREFERRED EMBODIMENTS

The new approach provided by this invention is for the characterization and measurement of trace amounts of organic molecules in water. It provides an analytical method for the detection and measurement of carbonyl compounds in aqueous solutions.

Radioactive derivatives of ammonia having high specific activities are used to label carbonyl compounds. The labeled compound is isolated and measured for radioactivity. The sensitivity (limits of detection) of this process are determined by the specific activity of the derivative.

The aqueous solutions containing the suspected or unknown trace amounts of carbonyl compounds are mixed with radioactive derivatives of ammonia. The carbonyl compounds, if present, stoichiometrically react with the derivatives of ammonia.

The weight of the parent compound, the carbonyl compound, is calculated from the radioactivity of the product resulting from the mixture of the suspected or unknown carbonyl compound and the radioactive derivatives of ammonia and the specific activity of the radioactive derivatives of ammonia.

The product of the aforesaid mixture is separated from the reaction mixture by chromatography or electrophoresis. The identity of the trace amounts of carbonyl compounds, if unknown or suspected, can be determined from the characteristic chromatographic or electrophoretic mobility of the derivative (the product of the mixing of the carbonyl compounds and the radioactive derivatives of ammonia).

The sensitivity of the method described hereinbefore is determined by specific activity of the radioactive chemical (radioactive derivatives of ammonia).

A specific embodiment is given below for the method of this invention.

In a typical reaction, 1 ml of aqueous solution containing $10^{-6}$–$10^{-9}$ mole of methyl ethyl ketone is mixed with 10 ml of acetic acid containing $10^{-5}$ mole of phenylhydrazine acetate, specific activity 50 micro curie/micro mole. The reaction mixture is allowed to stand at room temperature for 24 hours. The product is extracted from the reaction mixture with three 1 ml aliquots of ethyl ether following conversion of the acetic acid to sodium acetate with 1 normal sodium hydroxide. The extract is washed with 5 ml of saturated sodium chloride solution and dried by filtration through sodium sulfate. The extract is evaporated to approximately 50 micro liters in a nitrogen atmosphere then quantitively transfered to a Silica Gel G thin layer plate. Standards of the appropriate hydrazone, 1-5 micrograms, are applied to adjacent lanes. The standards serve as reference markers for the test compound. The plate is developed in the solvent solution 50 ml benzene: 50 ml pentane. The zone containing the product is quantitively transfered to a scintillation vial containing scintillation fluid and measured for radioactivity.

A sample calculation is given for the ideal system wherein 1 dpm=1 cpm and zero quenching, and the specific activity of the hydrazine=50 microcurie/micromole. When 1 curie=$10^{12}$ cpm, 1 mole of hydrazine contains $5 \times 10^{13}$ cpm. Thus 1 cpm=$2 \times 10^{-14}$ mole. For the methyl ethyl ketone reaction described above, $5 \times 10^4$ cpm=$10^{-9}$ moles ketone in the aqueous solution; $5 \times 10^7$ cpm=$10^{-6}$ moles of ketone in the aqueous solution.

For clarity, the following definitions of terms are provided:

(1) Aldehydes and ketones mean any chemical or chemicals in a mixture containing carbonyl groups. The concept also includes any chemical that can be converted to an aldehyde or ketone or derivatized by a molecule to yield a product containing a free carbonyl group.

(2) The meaning of the term "derivative of ammonia" includes but is not limited to hydrazine, phenylhydrazine, substituted phenyl hydrazine, hydroxylamine, and semicarbazides. The substituted phenylhydrazines mean that the ring may contain one or more electron withdrawing groups such as dinitrophenylhydrazine.

(3) Radioactive derivative includes molecules containing isotopes of carbon, hydrogen, nitrogen, halide or other gamma or beta emitting atoms.

(4) Aqueous solution means any sample of water, sewage, or biological fluid.

(5) Chromatographic mobility refers to the migration of the chemical on a support material. The migration depends on the interaction of the chemical with the support material and an organic solvent, an aqueous solvent, an electric field, or combinations of solvents and electric fields. The definition includes liquid, gas, thin layer, and paper chromatography, and electrophoresis. The definition specifically includes high pressure liquid chromatography.

(6) The measurement of radioactivity means the quantitive measurement of alpha, beta, and/or gamma emission by the radioactive derivative with or without the sepatating media.

I claim:

1. An analytical method for the detection and measurement of carbonyl compounds in aqueous solutions which comprises:
   reacting carbonyl compounds contained in an aqueous solution with a radioactive derivative of ammonia;
   separating the reaction product; and
   measuring the amount of said reaction product by a radioactive measurement to determine the amount of carbonyl compound present in said aqueous sample.

2. The analytical method recited in claim 1, wherein said carbonyl compound is an aldehyde.

3. The analytical method recited in claim 1 wherein said carbonyl compound is a ketone.

4. The analytical method recited in claim 1, wherein said radioactive measurement to determine the amount of carbonyl compound is calculated from the radioactivity of said reaction product and the specific activity of said radioactive derivative of ammonia.

5. The analytical method recited in claim 1 and additionally, the product is separated from the reaction mixture by chromatography, said product, when of unknown identity, being determined from the characteristic chromatographic mobility of the derivative.

6. The analytical method recited in claim 1 and additionally, the product is separated from the reaction mixture by electrophoresis, said product, when of unknown identity, being determined from the characteristic electrophoretic mobility of the derivative.

7. The analytical method recited in claim 1 and additionally, the sensitivity of the method being determined by the specific activity of the radioactive chemical.

* * * * *